(12) United States Patent
Seethamraju et al.

(10) Patent No.: US 10,670,684 B2
(45) Date of Patent: Jun. 2, 2020

(54) FREE-BREATHING NON-CONTRAST MR ANGIOGRAPHY

(71) Applicants: Siemens Healthcare GmbH, Erlangen (DE); The Brigham and Women's Hospital, Inc., Boston, MA (US)

(72) Inventors: Ravi Teja Seethamraju, Malden, MA (US); Ritu Randhawa Gill, Lexington, MA (US)

(73) Assignees: Siemens Healthcare GmbH, Erlangen (DE); The Brigham and Women's Hospital, Inc., Boston, MA (US)

( * ) Notice: Subject to any disclaimer, the term of this patent is extended or adjusted under 35 U.S.C. 154(b) by 575 days.

(21) Appl. No.: 14/989,028

(22) Filed: Jan. 6, 2016

(65) Prior Publication Data
US 2017/0192074 A1 Jul. 6, 2017

(51) Int. Cl.
| | | |
|---|---|---|
| *A61B 5/055* | (2006.01) | |
| *G01R 33/563* | (2006.01) | |
| *A61B 5/00* | (2006.01) | |
| *G01R 33/385* | (2006.01) | |
| *G01R 33/50* | (2006.01) | |

(52) U.S. Cl.
CPC ........ *G01R 33/5635* (2013.01); *A61B 5/0044* (2013.01); *A61B 5/055* (2013.01); *G01R 33/385* (2013.01); *G01R 33/50* (2013.01)

(58) Field of Classification Search
None
See application file for complete search history.

(56) References Cited

U.S. PATENT DOCUMENTS

| | | | |
|---|---|---|---|
| 7,020,509 B2 | 3/2006 | Held | |
| 8,452,065 B2 | 5/2013 | Azar et al. | |
| 8,744,551 B2 | 6/2014 | Koktzoglou et al. | |
| 2010/0232667 A1 | 9/2010 | Azar et al. | |
| 2011/0199082 A1* | 8/2011 | Kimura | A61B 5/0263 324/306 |

(Continued)

FOREIGN PATENT DOCUMENTS

WO 2014/085288 A1 6/2014

OTHER PUBLICATIONS

Amano, "Noncontrast-Enhanced Three-Dimensional Magnetic Resonance Aortography of the Thorax at 3.0 T Using Respiratory-Compensated T1-Weighted k-Space Segmented Gradient-Echo Imaging with Radial Data Sampling", Investigative Radiology, vol. 44, No. 9, Sep. 2009.*

(Continued)

*Primary Examiner* — Jonathan Cwern

(57) ABSTRACT

A system includes acquisition of a predetermined number of three-dimensional sub-frames from patient tissue using a T1-weighted radial sampling sequence and without contrast agent, determination of a matching one of a plurality of the three-dimensional images reconstructed from respective subsets of the predetermined number of three-dimensional sub-frames, based on a first three-dimensional image reconstructed from a first-acquired one of the predetermined number of three-dimensional sub-frames, and subtraction of the matching one of the plurality of the three-dimensional images from the first three-dimensional image to generate a second three-dimensional image.

18 Claims, 4 Drawing Sheets

(56) References Cited

U.S. PATENT DOCUMENTS

| | | | | |
|---|---|---|---|---|
| 2014/0103928 A1* | 4/2014 | Grodzki | ............ | G01R 33/4816 324/309 |
| 2015/0272453 A1* | 10/2015 | Heberlein | ............ | A61B 5/0263 600/419 |

OTHER PUBLICATIONS

Fuchs, Friedrich et al., "TrueFISP—technical considerations and cardiovascular applications", European Journal of Radiology, 46 (2003), DOI: 10.1016/S0720-048X(02)00330-3, (pp. 28-32, 5 total pages).

Gill, Ritu R. et al., "Diffusion-Weighted MRI of Malignant Pleural Mesothelioma: Preliminary Assessment of Apparent Diffusion Coefficient in Histologic Subtypes", Cardiopulmonary Imaging Original Research, Aug. 2010, DOI:10.2214/AJR.09.3519, downloaded from www.ajronline.org on Jul. 8, 2015. (pp. 125-130, 6 total pages).

Winkelmann, Stefanie et al., "An Optimal Radial Profile Order Based on the Golden Ratio for Time-Resolved MRI", IEEE Transactions on Medical Imaging, vol. 26, No. 1, Jan. 2007, DOI:10.1109/TMI.2006.885337, (pp. 68-76, 9 total pages).

Feng, Li et al., "Golden-Angle Radial Sparse Parallel MRI: Combination of Compressed Sensing, Parallel Imaging, and Golden-Angle Radial Sampling for Fast and Flexible Dynamic Volumetric MRI", [no date], 29pgs.

Block, Kai Tobias et al., "Towards Routine Clinical Use of Radial Stack-of-Stars 3D Gradient-Echo Sequences for Reducing Motion Sensitivity", Journal of the Korean Society of Magnetic Resonance in Medicine, 18(2), 2014, pISSN:1226-9751 / eISSN 2288-3800, http://dx.doi.org/10.13104/jksmrm.2014 Feb. 18, 1987, (pp. 87-106, 20 total pages).

Zhang, Tao et al., "Fast Pediatric 3D Free-Breathing Abdominal Dynamic Contrast Enhanced MRI With High Spatiotemporal Resolution", Journal of Magnetic Resonance Imaging, 41, (2015), DOI:10.1002/jmri.24551, (pp. 460-473, 14 total pages).

Rosenkrantz, Andrew B. et al., "Dynamic Contrast-Enhanced MRI of the Prostate With High Spatiotemporal Resolution Using compressed Sensing, Parallel Imaging, and Continuous Golden-Angle Radial Sampling: Preliminary Experience", Journal of Magnetic Resonance Imaging, 41, (2015), DOI:10.1002/jmri.24661, (pp. 1365-1373, 9 total pages).

Song, Hee Kwon et al., "Dynamic MRI With Projection Reconstruction and KWIC Processing for Simultaneous High Spatial and Temporal Resolution", Magnetic Resonance in Medicine, 52, (2004), DOI:10.1002/mrm.20237, (pp. 815-824, 10 total pages).

Song, Hee Kwon et al., "Noncontrast Enhanced Four-Dimensional Dynamic MRA with Golden Angel Radial Acquisition and K-space Weighted Image Contr4ast (KWIC) Reconstruction", Magnetic Resonance in Medicine 00, (2013), DOI:10.1002/mrm.25057, (pp. 1-11, 11 total pages).

Chandarana, Hersh et al., "Free-Breathing Contrast-Enhanced Multiphase MRI of the Liver Using a Combination of Compressed Sensing, Parallel Imaging, and Golden-Angle Radial Sampling", NIH Public Access Author Manuscript, Invest Radiol., Jan. 2013, 48(1), DOI:10.1097/RLI.0b013e318271869c, 17pgs.

Kawaji, Keigo et al., "Whole Heart Coronary Imaging with Flexible Acquisition Window and Trigger Delay", PLOS ONE, Feb. 26, 2015, DOI:10.1371/journal.pone.0112020, (1-14, 14 total pages).

Herborn, Christoph et al., "Evaluation of Steady state free precession imaging of the pancreas", Eur Radiol, 15, (2005), DOI:10.1007/s00330-005-2774-1, (pp. 1629-1633, 5 total pages).

Carr, H. Y. "Steady-State Free Precession in Nuclear Magnetic Resonance", Physical Review, vol. 112, No. 5, Dec. 1, 1958, (pp. 1693-1708, 16 total pages).

Herborn, Christoph U. et al., MRI of the Liver: Can True FISP Replace HASTE?, Journal of Magnetic Resonance Imaging, 17, (2003), DOI:10.1002/jmri.10248, (pp. 190-196, 7 total pages).

Numminen, Kirsti et al., "Magnetic Resonance Imaging of the Liver: True Fast Imaging with Steady State Free Precession Sequence Facilitates Rapid and Reliable Distinction Between Hepatic Hemangiomas and Liver Malignancies", Journal of Computer Assisted Tomography, vol. 27, No. 4, 2003, (pp. 571-576, 6 total pages).

Xie, Jingsi et al., "3D Flow-Independent Peripheral Vessel Wall Imaging Using T2-Prepared Phase-Sensitive Inversion-Recovery Steady-State Free Precession", Journal of Magnetic Resonance Imaging, 32, (2010), DOI:10.1002/jmri.22272, (pp. 399-408, 10 total pages).

Vasanawala, Shreyas S. et al., "Linear Combination Steady-State Free Precession MRI", Magnetic Resonance in Medicine, 43, (2000), (pp. 82-90, 9 total pages).

Bangerter, Neal K. et al., "Analysis of Multiple-Acquisition SSFP", Magnetic Resonance in Medicine, 51, (2004), DOI:10.1002/mrm.20052, (pp. 1038-1047, 10 total pages).

Xue, Hui et al., "Phase-Sensitive Inversion Recovery for Myocardial T1 Mapping with Motion Correction and Parametric Fitting", Magn Reson Med. Author Manuscript, May 2013, vol. 69, No. 5, DOI:10.1002/mrm.24385, (pp. 1408-1420, 24 total pages).

Kellman, Peter et al., "High Spatial and Temporal Resolution Cardiac Cine MRI from Retrospective Reconstruction of Data Acquired in Real Time Using Motion Correction and Resorting", Magnetic Resonance in Medicine, 62, (2009), DOI:10.1002/mrm.22153, (pp. 1557-1564, 8 total pages).

Stanisz, Greg J. et al., "T1, T2 Relaxation and Magnetization Transfer in Tissue at 3T", Magnetic Resonance in Medicine, 54, (2005), DOI:10.1002/mrm.20605, (pp. 507-512, 6 total pages).

* cited by examiner

FREE-BREATHING NON-CONTRAST MR ANGIOGRAPHY

BACKGROUND

Magnetic resonance angiography (MRA) uses the nuclear magnetic resonance phenomenon to produce images of patient vasculature. According to some MRA techniques, a contrast agent such as gadolinium is injected into a patient prior to image acquisition and a series of magnetic resonance (MR) images are acquired as the contrast agent perfuses into the tissues of interest. However, common contrast agents have been linked to nephrogenic systemic fibrosis (NSF) and their usage is therefore widely discouraged.

Techniques for non-contrast MRA exist but are susceptible to patient motion. Accordingly, these techniques require external triggering (e.g., ECG, respiratory, etc.) or require a patient to remain still and hold his breath during image acquisition. Moreover, these techniques typically acquire only a single two-dimensional slice image in a given acquisition sequence.

Efficient and effective techniques for free-breathing, non-contrast, non-triggered three-dimensional MRA are desired.

DETAILED DESCRIPTION

The following description is provided to enable any person in the art to make and use the described embodiments. Various modifications, however, will remain readily apparent to those in the art.

A brief description of image acquisition using the NMR phenomenon will now be provided. If a substance such as human tissue is subjected to a uniform magnetic field (i.e., polarizing field $B_0$), the individual magnetic moments of the nuclear spins in the tissue attempt to align with this polarizing field but precess about the field in random order at their characteristic Larmor frequency. Usually the nuclear spins comprised of hydrogen atoms are desired for clinical imaging, but other NMR-active nuclei are also occasionally used. A net magnetic moment $M_z$ is produced in the direction of the polarizing field, and the randomly-oriented magnetic components in the perpendicular, or transverse, plane (x-y plane) cancel one another.

If, however, the substance is subjected to a magnetic field which is in the x-y plane (i.e., excitation field $B_1$; also referred to as a radiofrequency (RF) field) and which is near the Larmor frequency, the net aligned moment, $M_z$, may be rotated, or "tipped" into the x-y plane to produce a net transverse magnetic moment $M_t$, which is rotating, or spinning, in the x-y plane at the Larmor frequency. A signal is emitted by the excited spins after the excitation field $B_1$ is terminated. The emitted signals are detected, digitized and processed to reconstruct an image using one of many well-known MR reconstruction techniques.

Figure 1:
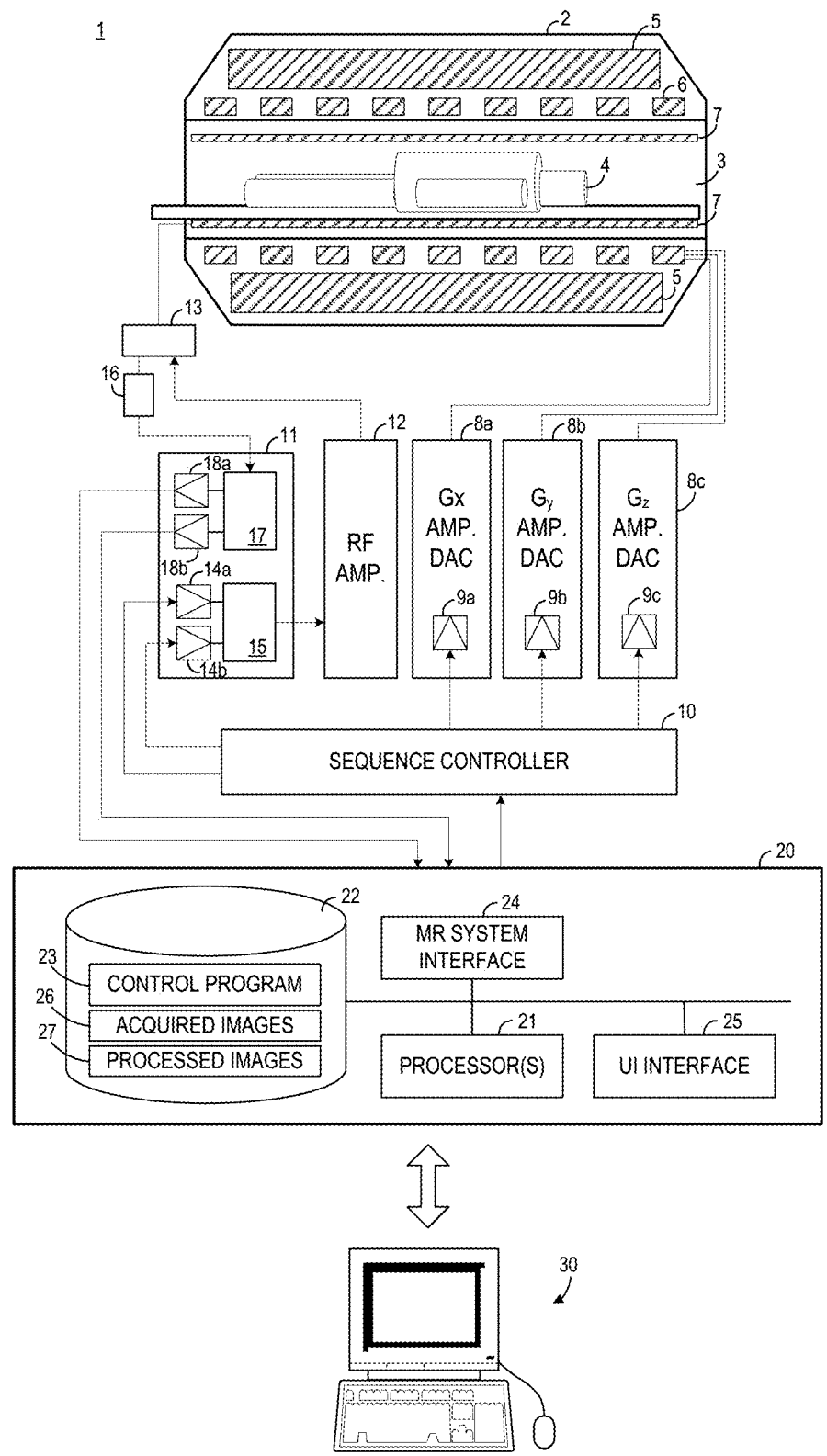
FIG. 1 is a block diagram of an MRA system according to some embodiments.

FIG. 1 illustrates magnetic resonance imaging (MRI) system 1 according to some embodiments. MRI system 1 includes MRI chassis 2, which defines bore 3 in which patient 4 is disposed. MRI chassis 2 includes polarizing main magnet 5, gradient coils 6 and RF coil 7 arranged about bore 3. According to some embodiments, polarizing main magnet 5 generates the uniform magnetic field $B_0$ mentioned above and RF coil 7 emits the excitation field $B_1$.

Gradient coils 6 produce magnetic field gradients $G_x$, $G_y$, and $G_z$ which are used for position-encoding NMR signals. The magnetic field gradients $G_x$, $G_y$, and $G_z$ distort the main magnetic field in a predictable way so that the Larmor frequency of nuclei within the main magnetic field varies as a function of position. Accordingly, an excitation field $B_1$ which is near a particular Larmor frequency will tip the net aligned moment $M_z$ of those nuclei located at field positions which correspond to the particular Larmor frequency, and signals will be emitted only by those nuclei after the excitation field $B_1$ is terminated.

Gradient coils 6 may consist of three windings, for example, each of which is supplied with current by an amplifier 8a-8c in order to generate a linear gradient field in its respective Cartesian direction (i.e., x, y, or z). Each amplifier 8a-8c includes a digital-analog converter 9a-9c which is controlled by a sequence controller 10 to generate desired gradient pulses at proper times.

Sequence controller 10 also controls the generation of RF pulses by RF system 11. RF system 11 is responsive to a scan prescription and direction from sequence controller 10 to produce RF pulses of the desired frequency, phase, and pulse amplitude waveform. The generated RF pulses may be applied to the whole of RF coil 7 or to one or more local coils or coil arrays. RF coil 7 converts the RF pulses emitted by RF amplifier 12, via multiplexer 13, into a magnetic alternating field in order to excite the nuclei and align the nuclear spins of the object to be examined or the region of the object to be examined.

The RF pulses to be produced by RF system 11 are represented digitally as complex numbers. Sequence controller 10 supplies these numbers in real and imaginary parts to digital-analog converters 14a-14b in RF system 11 to create corresponding analog pulse sequences. Transmission channel 15 modulates the pulse sequences with a radio-frequency carrier signal having a base frequency corresponding to the resonance frequency of the nuclear spins in the volume to be imaged.

RF coil 7 both emits the radio-frequency pulse to excite nuclear spins and scans the alternating field which is produced as a result of the precessing nuclear spins, i.e. the nuclear spin echo signals. The received signals are received by multiplexer 13, amplified by RF amplifier 16 and demodulated in receiving channel 17 of RF system 11 in a phase-sensitive manner. Analog-digital converters 18a and 18b convert the demodulated signals into a real part and an imaginary part.

Computing system 20 receives the real and imaginary parts and reconstructs an image therefrom according to known techniques. System 20 may comprise any general-purpose or dedicated computing system. Accordingly, system 20 includes one or more processing units 21 (e.g., processors, processor cores, execution threads, etc.) configured to execute processor-executable program code to cause system 20 to operate as described herein, and storage device 22 for storing the program code. Storage device 22 may comprise one or more fixed disks, solid-state random access memory, and/or removable media (e.g., a thumb drive) mounted in a corresponding interface (e.g., a USB port).

Storage device 22 stores program code of control program 23. One or more processing units 21 may execute control program 23 to cause system 20 to perform any one or more of the processes described herein. For example, one or more processing units 21 may execute control program 23 to cause system 20 to receive the real and imaginary parts of a received RF signal via MR system interface 24 and reconstruct an image therefrom according to known techniques. Such an image may be stored among acquired images 26 of storage device 22. Control program 23 may also be executed to process one or more reconstructed images as described herein, and to store a processed image among processed images 27 of storage device 22.

One or more processing units 21 may also execute control program 23 to provide instructions to sequence controller 10 via MR system interface 24. For example, sequence controller 10 may be instructed to initiate the desired pulse sequences and corresponding scanning of k-space (i.e., acquired signal data). In particular, sequence controller 10 may be instructed to control the switching of magnetic field gradients via amplifiers 8a-8c at appropriate times, the transmission of radio-frequency pulses having a defined phase and amplitude via RF system 11 and RF amplifier 12, and the reception of the resulting magnetic resonance signals.

Acquired images 26 and/or processed images 27 may be provided to terminal 30 via UI interface 25 of system 20. UI interface 25 may also receive input from terminal 30, which may be used to provide commands to control program 23 in order to control sequence controller 10 other elements of system 1. Terminal 30 may simply comprise a display device and an input device coupled to system 20. In some embodiments, terminal 30 is a separate computing device such as, but not limited to, a desktop computer, a laptop computer, a tablet computer, and a smartphone.

Each element of system 1 may include other elements which are necessary for the operation thereof, as well as additional elements for providing functions other than those described herein. Storage device 22 may also store data and other program code for providing additional functionality and/or which are necessary for operation of system 20, such as device drivers, operating system files, etc.

Figure 2:
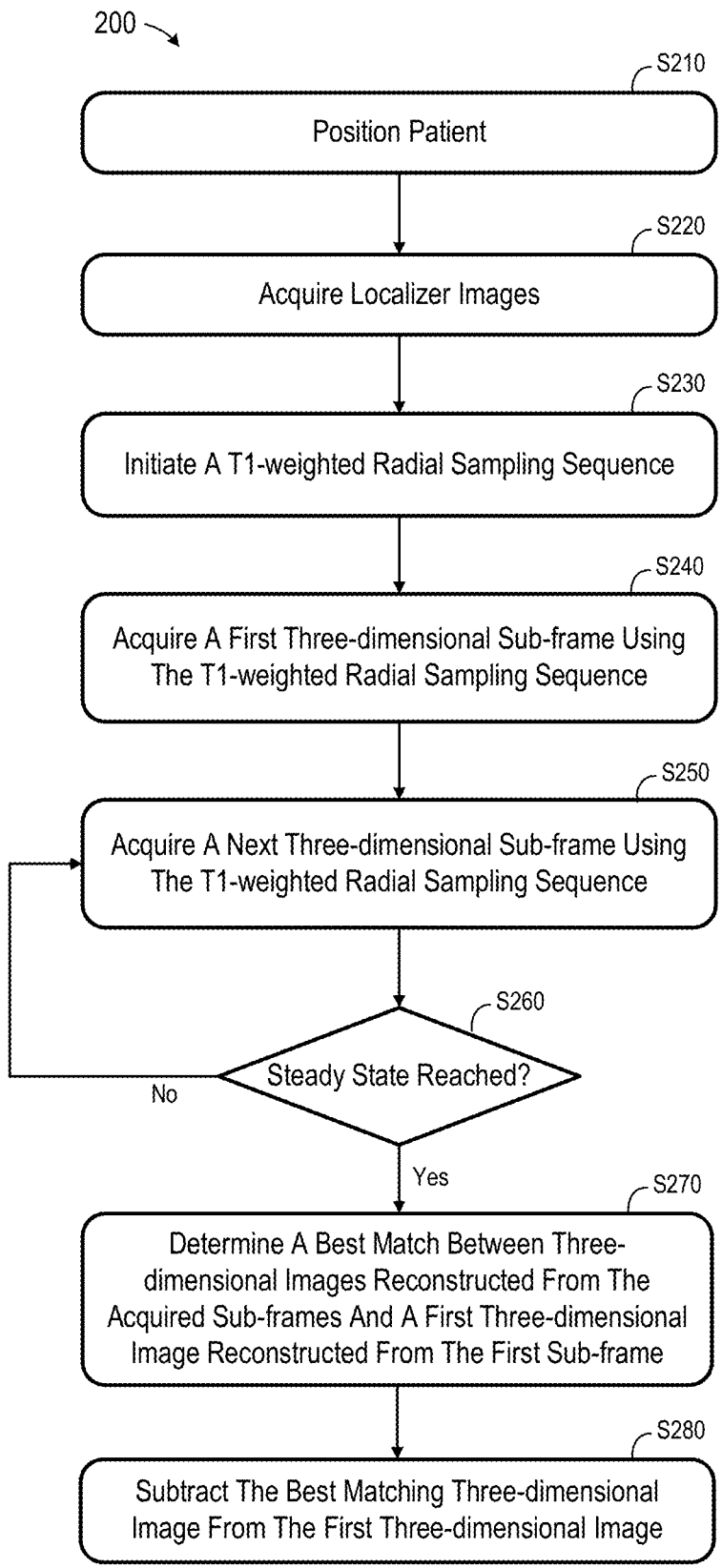
FIG. 2 is a flow diagram of a process according to some embodiments.

FIG. 2 is a flowchart of process 200 according to some embodiments. Some embodiments of process 200 provide free-breathing, non-contrast, non-triggered three-dimensional MRA.

In some embodiments, various hardware elements of system 1 (e.g., one or more processors) execute program code to perform process 200. Process 200 and all other processes mentioned herein may be embodied in processor-executable program code read from one or more of non-transitory computer-readable media, such as a floppy disk, a disk-based or solid-state hard drive, CD-ROM, a DVD-ROM, a Flash drive, and a magnetic tape, and then stored in a compressed, uncompiled and/or encrypted format. In some embodiments, hard-wired circuitry may be used in place of, or in combination with, program code for implementation of processes according to some embodiments. Embodiments are therefore not limited to any specific combination of hardware and software.

Initially, at S210, a patient is positioned for imaging within an MRI device. For example, FIG. 1 illustrates patient 4 positioned within bore 3 of MRI chassis 2. Positioning of the patient may be performed using known techniques, and the patient position may be dependent upon the volume of the patient to be imaged. According to some embodiments, receiver RF coils are arranged around the volume of interest.

Next, localizer images are acquired at S220 according to known protocols. The localizer images are acquired using the NMR phenomenon as described above. The localizer images comprise one or more planes, typically a set of three planes, to obtain an orthographic location of the organ to be imaged. These localizer images are used for plotting positions of the acquisitions of S230-S250.

In this regard, a predetermined number of three-dimensional acquisitions, or sub-frames, are acquired at S230 through S250 using a T1-weighted radial sampling sequence. More specifically, after initiating such a sequence at S230 according to known techniques, a first sub-frame is acquired at S240 and one less than the predetermined number of sub-frames are acquired at S250.

The predetermined number may be a number whose total acquisition time is expected to be greater than the time required for the imaged tissue to reach steady-state (i.e., a state in which the nuclei spins are realigned with the main magnetic field $B_0$). According to some embodiments, the predetermined number is five. The predetermined number may be is dependent on the parameters of the individual acquisition and the time for the spins in the blood to reach steady state. The sequence of gradient pulses, RF pulses and RF scanning required for acquisition of each sub-frame may be controlled by sequence controller 10 under command of device 20, using any techniques which are or become known for acquiring three-dimensional sub-frames using a T1-weighted radial sampling sequence.

In a T1-weighted sampling sequence, the scanning parameters TR (repetition time) and TE (echo time) are set to small values (i.e., short times) to minimize the effect of T2 relaxation effects, such that the resulting image is influenced primarily by T1 relaxation effects. T1-relaxation refers to the longitudinal relaxation of a tissue's net magnetization vector. More specifically, spins aligned in an external field (e.g., $B_0$) are put into the transverse plane by an RF pulse. The spins slide back toward the original equilibrium of $B_0$, but not all tissues get back to the original equilibrium equally quickly, and a tissue's T1 reflects the amount of time its protons' spins take to realign with the main magnetic field ($B_0$). Fat quickly realigns its longitudinal magnetization with $B_0$, and fat therefore appears bright in a T1-weighted image. Conversely, water exhibits a slower longitudinal magnetization realignment after an RF pulse and appears dark.

A radial sampling sequence is relatively robust to motion artifacts as artifacts are dispersed and appear less prominent when reconstructed. The radial sampling sequence of S230-S250 may comprise the known stack-of-stars sequence. The stack-of-stars sequence is a three-dimensional acquisition where radial samplings are performed to acquire the $k_x$-$k_y$ space, and traditional Cartesian phase-encoding is used in the slice-select ($k_z$) direction. In the current embodiment, such a three-dimensional radial phase-encoded sequence is implemented as a gradient-recalled echo (GRE) sequence.

Figure 3A:
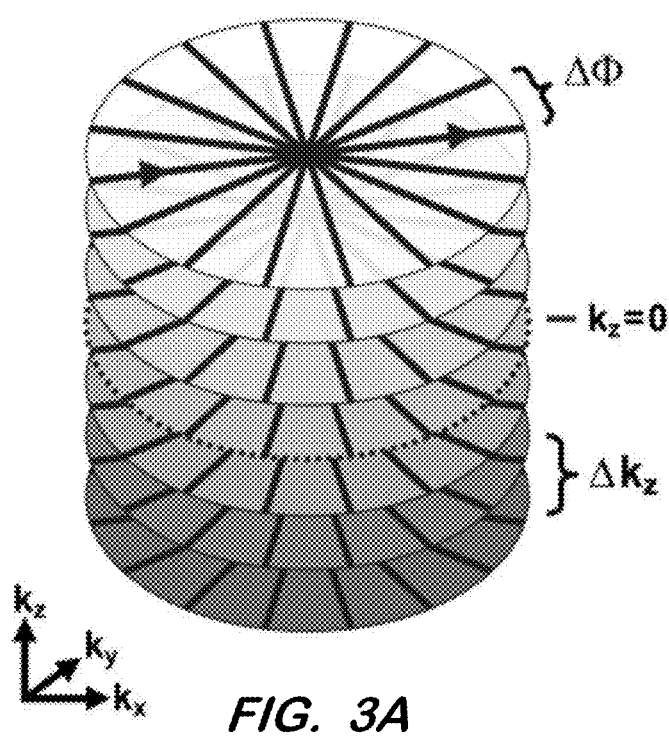
FIG. 3A illustrates a radial stack-of-stars sampling sequence according to some embodiments.

FIG. 3A depicts standard Cartesian phase-encoding in the slice-select (SLICE) direction, while in the $k_x$-$k_y$ space data are acquired along radial spokes that are rotated around the center, resulting in cylindrical k-space coverage composed of stacked discs. According to some embodiments, the data is acquired by playing readout gradients in the $k_x$ and $k_y$ direction simultaneously and modulating the amplitudes according to: $G_{READ}=\sin(\Phi)$ and $G_{PHASE}=\cos(\Phi)$. The RF excitation and the gradient calculation in SLICE direction may follow a conventional three-dimensional GRE sequence.

In some embodiments, all phase-encoding steps along the SLICE direction ("partitions") are acquired sequentially before lines at different angular positions are acquired. This results in short periods of Cartesian sampling, data consistency within the spoke stacks, and motion robustness of radial sampling for the three-dimensional stack-of-stars geometry. The Cartesian phase-encoding steps may be performed from the center partition to the k-space periphery, or in linear order from $-k_{max}$ to $+k_{max}$. For the angular ordering, embodiments may employ equidistant angular sampling with multiple interleaves, a golden-angle sampling scheme, or other sampling.

Figure 3B:
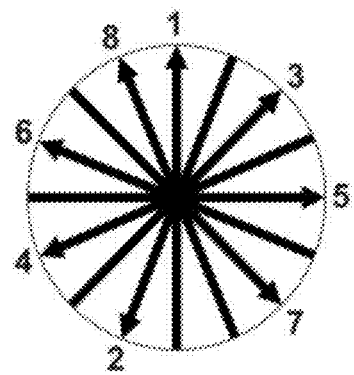
FIG. 3B illustrates a radial stack-of-stars sampling sequence according to some embodiments.

FIG. 3B illustrates the case of equidistant angular sampling with multiple interleaves. The angular distance is calculated according to $\Delta\Phi=180°/n_{total}$ where $n_{total}$ is the total number of spokes. Acquiring the spokes using multiple interleaves may be beneficial because the interleaving reduces temporal coherences in k-space, thereby spreading out motion inconsistencies in k-space and visually attenuating corresponding artifacts. In some embodiments $n_{rot}=8$ interleaves, where spokes have an angular distance of $n_{rot}=180° n_{rot}/n_{total}$ and subsequent interleaves are rotated by $\Delta\Phi$. Furthermore, the orientation of every second spoke may be alternated (i.e., 180° added to its rotation) so that adjacent spokes in k-space exhibit opposing orientation.

Figure 3C:
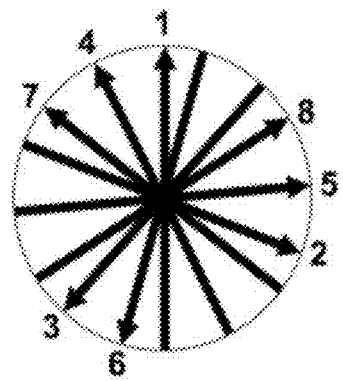
FIG. 3C illustrates a radial stack-of-stars sampling sequence according to some embodiments.

According to the golden-angle sampling scheme shown in FIG. 3C, the angle is increased each time by $\Delta\Phi GA=111.25°$, which corresponds to 180° multiplied by the golden ratio. Therefore, subsequently-sampled spokes always add complementary information while filling gaps within the previously-sampled spokes. As consequence, any sequential set of acquired spokes covers k-space substantially uniformly, which enables reconstruction of temporal sub-frames and is suitable for dynamic imaging studies. Additional interleaving or alternation of spokes is not needed for this scheme in some embodiments. The golden-angle acquisition scheme exhibits substantially uniform coverage of k-space for any arbitrary number of consecutive spokes, in particular if the arbitrary number belongs to the Fibonacci series (defined as $F(k+2)=F(k)+F(k+1)$, where $k>0$, and $F(0)=0$ and $F(1)=1$, e.g. 1, 2, 3, 5, 8, 13, 21, 34, . . . ). The high contrast resulting from blood in the earliest sub-frame occurs in the center of k-space while the definition of the anatomy occurs at the periphery. Accordingly, the information from the subsequent sub-frames acquired at S250 may facilitate the compensation of motion from earlier sub-frames, if any.

After the predetermined number of images have been acquired at S240 and S250, it is determined at S260 whether a steady state has been reached. This determination may be time-based (e.g., a determination of whether a certain time has elapsed since a last excitation RF pulse), based on a sensing of signals emitted by patient tissue (e.g., is the signal amplitude lower than a threshold value), based on an intensity level of a last-acquired image, or based on a combination of these and/or other factors. If it is determined that a steady state has not been reached, another three-dimensional sub-frame is acquired using the T1-weighted radial sampling sequence at S250, and flow returns to S260 to again determine whether a steady state has been reached.

Flow proceeds to S270 once it has been determined at S260 that a steady state has been reached. At S270, a first three-dimensional image reconstructed from the first acquired sub-frame is compared against three-dimensional images reconstructed from the first and second subframes, from the first second and third sub-frames, from the first, second, third and fourth sub-frames and so on in order to determine a best match (e.g., in which the contrast in the blood (i.e., the center of k-space) is the least). Any image comparison/matching algorithm may be utilized at S270, including but not limited to a simple time course obtained by averaging the center of k-space from the first sub-frame to the last sub-frame to reveal a decay of the signal in the blood.

Reconstruction may employ any type of processing that is or becomes known, such as a KWIK-like reconstruction technique which employs K-space information from multiple frames to compensate for motion. In some embodiments, the data are reconstructed using a radial k-t SPARSE-SENSE method as described by Chandarana H., Feng L., Block T K., et al., in "Free-breathing contrast-enhanced multiphase MRI of the liver using a combination of compressed sensing, parallel imaging, and golden-angle radial sampling", Invest. Radiol. 2013; 48:10-16. This method combines compressed sensing and parallel imaging to take advantage of the spatial-encoding capabilities of the phased-array receiver coil and the redundancies in the acquired time-series of data, in order to enable reconstruction of dynamic frames with high temporal resolution.

Figure 4A:
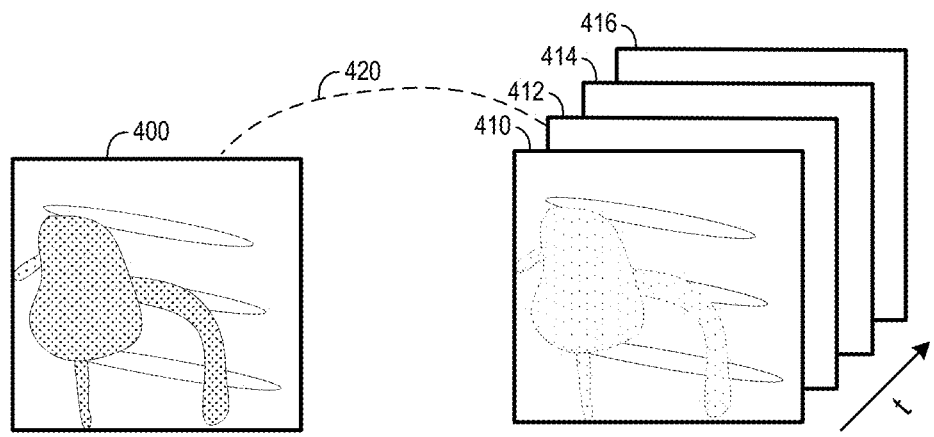
FIG. 4A illustrates processing of acquired MR images according to some embodiments.

At S280, the best matching three-dimensional image reconstructed from a subset of sub-frames is subtracted from the first three-dimensional image reconstructed from the first acquired sub-frame. FIG. 4A depicts S280 according to some embodiments. Although depicted in two dimensions, image 400 is an example of the first three-dimensional image reconstructed from the first sub-frame acquired at S240. Similarly, images 410 through 416 are three-dimensional images reconstructed from sub-frames acquired at S250. Dashed line 420 indicates that image 412 has been determined to be the best-matching image at S270.

Figure 4B:
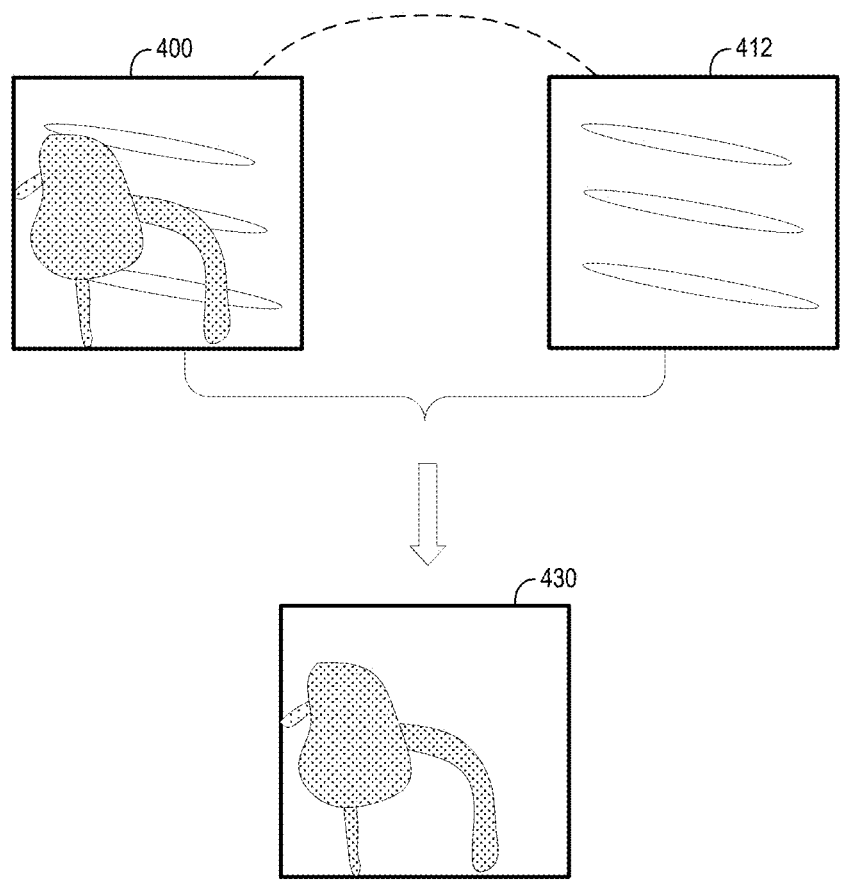
FIG. 4B illustrates processing of acquired MR images according to some embodiments.

Next, at S280, the best-matching image is subtracted from the first image to determine a new image. According to some embodiments, the new image may comprise a set of pixel intensity values, where each value is equal to a difference between an intensity value of a pixel of the first image and an intensity value of a correspondingly-located pixel of the best-matching image. FIG. 4B depicts subtraction of best-matching image 412 from first image 400 to generate new three-dimensional image 430. The generated three-dimensional image may simply consist of the aforementioned set of pixel intensity values. In some embodiments, the set of pixel intensity values is subjected to known image processing to smooth, filter, enhance or otherwise improve the generated image for its intended purpose.

Some embodiments provide efficient free-breathing, non-contrast, non-triggered three-dimensional MRA. According to some embodiments, vasculature appears bright in the first-acquired image and less bright in subsequent images. The difference between the first-acquired image and the subsequent images therefore represents vascular structure and may be used to generate an image of vascular structure. Registration between the first-acquired image and the best-matching image may be avoided because the best-matching determination implicitly identifies the best-registered image.

The foregoing diagrams represent logical architectures for describing processes according to some embodiments, and actual implementations may include more or different components arranged in other manners. Other topologies may be used in conjunction with other embodiments. Moreover, each component or device described herein may be implemented by any number of devices in communication via any number of other public and/or private networks. Two or more of such computing devices may be located remote from one another and may communicate with one another via any known manner of network(s) and/or a dedicated connection. Each component or device may comprise any number of hardware and/or software elements suitable to provide the functions described herein as well as any other functions. For example, any computing device used in an implementation of a system according to some embodiments may include a processor to execute program code such that the computing device operates as described herein.

Embodiments described herein are solely for the purpose of illustration. Those in the art will recognize other embodiments may be practiced with modifications and alterations to that described above.

What is claimed is:

1. A system comprising:
   a chassis defining a bore;
   a main magnet to generate a polarizing magnetic field within the bore;
   a gradient system to apply a gradient magnetic field to the polarizing magnetic field;
   a radio frequency system to apply an excitation pulse to patient tissue disposed within the bore and to receive signals from the patient tissue; and
   a computing system to receive the signals from the radio frequency system, the computing system to execute program code to:
   control the gradient system and the radio frequency system to acquire a predetermined number of three-dimensional sub-frames from the patient tissue using a T1-weighted radial sampling sequence and while contrast agent is not present in the patient tissue;
   reconstruct a first three-dimensional image from a first-acquired one of the predetermined number of three-dimensional sub-frames;
   reconstruct a plurality of three-dimensional images from respective sequentially-acquired subsets of the predetermined number of three-dimensional sub-frames, where each sequentially-acquired subset includes the first-acquired one of the predetermined number of three-dimensional sub-frames;
   determine one of the plurality of three-dimensional images reconstructed from respective sequentially-acquired subsets of the predetermined number of three-dimensional sub-frames in which a blood-related signal strength is most similar to a blood-related signal strength in the first three-dimensional image reconstructed from the first-acquired one of the predetermined number of three-dimensional sub-frames; and
   subtract the determined one of the plurality of the three-dimensional images from the first three-dimensional image to generate a second three-dimensional image.

2. A system according to claim 1, where the T1-weighted radial sampling sequence includes acquisition of radial samples, and where an angle between successive radial samples is 111.25°.

3. A system according to claim 2, the computing system to execute program code to:
   determine, after control of the gradient system and the radio frequency system to acquire the predetermined number of three-dimensional sub-frames, whether the patient tissue has reached a steady state; and
   if it is determined that the patient tissue has not reached a steady state, control the gradient system and the radio frequency system to acquire another three-dimensional sub-frame from the patient tissue using a T1-weighted radial sampling sequence while contrast agent is not present in the patient tissue,
   wherein the plurality of three-dimensional images are reconstructed from respective subsets of the predetermined number of three-dimensional sub-frames and the another three-dimensional sub-frame.

4. A system according to claim 1, where the T1-weighted radial sampling sequence includes acquisition of radial samples, and where an angle between successive radial samples is $\Delta\Phi=180°/n_{total}$, where $n_{total}$ is the total number of radial samples.

5. A system according to claim 1, the computing system to execute program code to:
   determine, after control of the gradient system and the radio frequency system to acquire the predetermined number of three-dimensional sub-frames, whether the patient tissue has reached a steady state; and
   if it is determined that the patient tissue has not reached a steady state, control the gradient system and the radio frequency system to acquire another three-dimensional sub-frame from the patient tissue using a T1-weighted radial sampling sequence while contrast agent is not present in the patient tissue,
   wherein the plurality of three-dimensional images are reconstructed from respective subsets of the predetermined number of three-dimensional sub-frames and the another three-dimensional sub-frame.

6. A system according to claim 1, wherein acquisition of the predetermined number of three-dimensional sub-frames from the patient tissue occurs while the patient is free breathing.

7. A computer-implemented method for a system comprising a main magnet to generate a polarizing magnetic field, a gradient system to apply a gradient magnetic field to the polarizing magnetic field, and a radio frequency system to apply an excitation pulse to patient tissue disposed within the polarizing magnetic field and to receive signals from the patient tissue, the method comprising:
   controlling the gradient system and the radio frequency system to acquire a predetermined number of three-dimensional sub-frames from the patient tissue using a T1-weighted radial sampling sequence and while contrast agent is not present in the patient tissue;
   reconstructing a first three-dimensional image from a first-acquired one of the predetermined number of three-dimensional sub-frames;
   reconstructing a plurality of three-dimensional images from respective sequentially-acquired subsets of the predetermined number of three-dimensional sub-frames, where each sequentially-acquired subset includes the first-acquired one of the predetermined number of three-dimensional sub-frames;
   determining one of the plurality of three-dimensional images reconstructed from respective sequentially-acquired subsets of the predetermined number of three-dimensional sub-frames in which a blood-related signal strength is most similar to a blood-related signal strength in the first three-dimensional image reconstructed from the first-acquired one of the predetermined number of three-dimensional sub-frames; and subtracting the determined one of the plurality of the three-dimensional images from the first three-dimensional image to generate a second three-dimensional image.

8. A method according to claim 7, where the T1-weighted radial sampling sequence includes acquisition of radial samples, and where an angle between successive radial samples is 111.25°.

9. A method according to claim 8, further comprising:
determining, after controlling the gradient system and the radio frequency system to acquire the predetermined number of three-dimensional sub-frames, whether the patient tissue has reached a steady state; and
if it is determined that the patient tissue has not reached a steady state, controlling the gradient system and the radio frequency system to acquire another three-dimensional sub-frame from the patient tissue using a T1-weighted radial sampling sequence while contrast agent is not present in the patient tissue,
wherein the plurality of three-dimensional images are reconstructed from respective subsets of the predetermined number of three-dimensional sub-frames and the another three-dimensional sub-frame.

10. A method according to claim 7, where the T1-weighted radial sampling sequence includes acquisition of radial samples, and where an angle between successive radial samples is $\Delta\Phi=180°/n_{total}$, where $n_{total}$ is the total number of radial samples.

11. A method according to claim 7, further comprising:
determining, after controlling the gradient system and the radio frequency system to acquire the predetermined number of three-dimensional sub-frames, whether the patient tissue has reached a steady state; and
if it is determined that the patient tissue has not reached a steady state, controlling the gradient system and the radio frequency system to acquire another three-dimensional sub-frame from the patient tissue using a T1-weighted radial sampling sequence while contrast agent is not present in the patient tissue,
wherein the plurality of three-dimensional images are reconstructed from respective subsets of the predetermined number of three-dimensional sub-frames and the another three-dimensional sub-frame.

12. A method according to claim 7, wherein acquisition of the predetermined number of three-dimensional sub-frames from the patient tissue occurs while the patient is free breathing.

13. A non-transitory computer-readable medium storing program code, the program code executable by a computer system to cause the computer system to:
control a gradient system and a radio frequency system to acquire a predetermined number of three-dimensional sub-frames from patient tissue using a T1-weighted radial sampling sequence while contrast agent is not present in the patient tissue;
reconstruct a first three-dimensional image from a first-acquired one of the predetermined number of three-dimensional sub-frames;
reconstruct a plurality of three-dimensional images from respective sequentially-acquired subsets of the predetermined number of three-dimensional sub-frames, where each sequentially-acquired subset includes the first-acquired one of the predetermined number of three-dimensional sub-frames;
determine one of the plurality of three-dimensional images reconstructed from respective sequentially-acquired subsets of the predetermined number of three-dimensional sub-frames in which a blood-related signal strength is most similar to a blood-related signal strength in the first three-dimensional image reconstructed from the first-acquired one of the predetermined number of three-dimensional sub-frames; and
subtract the determined one of the plurality of the three-dimensional images from the first three-dimensional image to generate a second three-dimensional image.

14. A medium according to claim 13, where the T1-weighted radial sampling sequence includes acquisition of radial samples, and where an angle between successive radial samples is 111.25°.

15. A medium according to claim 14, the program code executable by a computer system to cause the computer system to:
determine, after controlling the gradient system and the radio frequency system to acquire the predetermined number of three-dimensional sub-frames, whether the patient tissue has reached a steady state; and
if it is determined that the patient tissue has not reached a steady state, controlling the gradient system and the radio frequency system to acquire another three-dimensional sub-frame from the patient tissue using a T1-weighted radial sampling sequence while contrast agent is not present in the patient tissue,
wherein the plurality of three-dimensional images are reconstructed from respective subsets of the predetermined number of three-dimensional sub-frames and the another three-dimensional sub-frame.

16. A medium according to claim 13, where the T1-weighted radial sampling sequence includes acquisition of radial samples, and where an angle between successive radial samples is $\Delta\Phi=180°/n_{total}$, where $n_{total}$ is the total number of radial samples.

17. A medium according to claim 13, the program code executable by a computer system to cause the computer system to:
determine, after controlling the gradient system and the radio frequency system to acquire the predetermined number of three-dimensional sub-frames, whether the patient tissue has reached a steady state; and
if it is determined that the patient tissue has not reached a steady state, controlling the gradient system and the radio frequency system to acquire another three-dimensional sub-frame from the patient tissue using a T1-weighted radial sampling sequence while contrast agent is not present in the patient tissue,
wherein the plurality of three-dimensional images are reconstructed from respective subsets of the predetermined number of three-dimensional sub-frames and the another three-dimensional sub-frame.

18. A medium according to claim 13, wherein acquisition of the predetermined number of three-dimensional sub-frames of the patient tissue using a T1-weighted radial sampling sequence occurs while the patient is free breathing.

* * * * *